United States Patent [19]

Kirsch et al.

[11] Patent Number: 5,665,716

[45] Date of Patent: Sep. 9, 1997

[54] 24-HOMO VITAMIN D DERIVATIVES, PROCESS FOR THEIR PRODUCTION AND PHARMACEUTICAL PREPARATIONS OBTAINED THEREFROM

[75] Inventors: Gerald Kirsch; Günter Neef; Katicia Schwarz; Matthias Bräutigam; Ruth Thieroff-Ekerdt; Petra Rach, all of Berlin, Germany

[73] Assignee: Schering Aktiengesellschaft, Berlin, Germany

[21] Appl. No.: 592,017

[22] Filed: Oct. 2, 1990

[30] Foreign Application Priority Data

Oct. 2, 1989 [DE] Germany .................. 39 33 034.6

[51] Int. Cl.[6] .................. A61K 31/59; C07C 401/00
[52] U.S. Cl. .................. 514/167; 552/653
[58] Field of Search .................. 204/157.67, 157.9, 204/158.87; 552/653; 514/167

[56] References Cited

U.S. PATENT DOCUMENTS

| | | | |
|---|---|---|---|
| 4,847,012 | 7/1989 | DeLuca et al. | 552/653 |
| 4,927,815 | 5/1990 | DeLuca et al. | 552/653 |
| 5,030,772 | 7/1991 | DeLuca et al. | 568/817 |
| 5,414,098 | 5/1995 | DeLuca et al. | 552/653 |
| 5,532,391 | 7/1996 | DeLuca et al. | 552/653 |

FOREIGN PATENT DOCUMENTS

| | | |
|---|---|---|
| 0 245 524 | 11/1986 | European Pat. Off. |
| WO 86/02078 | 4/1986 | WIPO |
| WO 89/10353 | 11/1989 | WIPO |

*Primary Examiner*—Kimberly J. Prior
*Attorney, Agent, or Firm*—Millen, White, Zelano, & Branigan, P.C.

[57] ABSTRACT

New 24-homo vitamin D derivatives of formula I

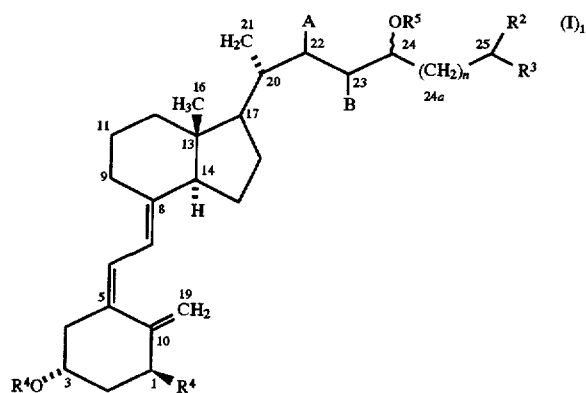

are described, in which $R^1$ means a hydrogen atom, a hydroxy, an alkanoyloxy group with 1 to 8 carbon atoms or an aralkanoyloxy group with up to 8 carbon atoms, $R^2$ and $R^3$, independently of one another, mean a linear or branched alkyl group with 1 to 4 carbon atoms, a trifluoromethyl group or together mean a saturated carbocyclic ring with 3 to 9 carbon atoms formed with carbon atom 25, $R^4$ and $R^5$, independently of one another, mean a hydrogen atom, an alkanoyl group with 1 to 8 carbon atoms or an aralkanoyl group with up to 8 carbon atoms, and A and B each mean a hydrogen or together a second bond, and n stands for 1, 2, 3, 4 or 5.

16 Claims, No Drawings

24-HOMO VITAMIN D DERIVATIVES, PROCESS FOR THEIR PRODUCTION AND PHARMACEUTICAL PREPARATIONS OBTAINED THEREFROM

BACKGROUND OF THE INVENTION

This invention relates to 24-homo vitamin D derivatives of formula I

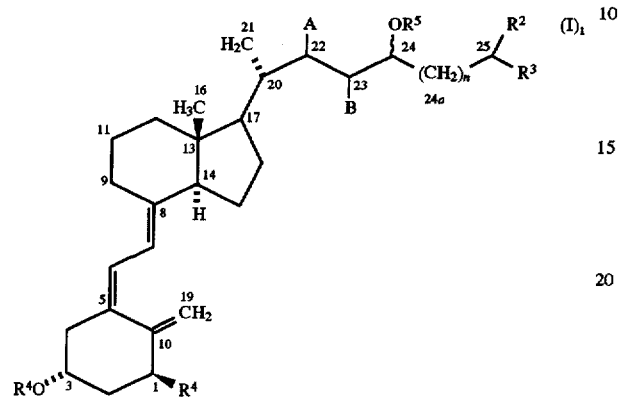

in which $R^1$ means a hydrogen atom, a hydroxy or an acyloxy group with 1 to 8 carbon atoms, $R^2$ and $R^3$, independently of one another, mean a linear or branched alkyl group exhibiting 1 to 4 carbon atoms, a trifluoromethyl group or together mean a saturated carbocyclic ring with 3 to 9 carbon atoms formed with carbon atom 25, $R^4$ and $R^5$, independently of one another mean a hydrogen atom or acyl group exhibiting 1 to 8 carbon atoms, and A and B each mean a hydrogen or together a second bond, n stands for 1, 2, 3, 4, or 5, as well as a process for their production, pharmaceutical preparations, which contain these compounds as well as their use for the production of pharmaceutical agents.

The acyloxy or acyl groups possible for the radicals $R^1$, $R^4$ and $R^5$ are especially derived from saturated carboxylic acids or also from benzoic acid.

If $R^2$ and $R^3$ form a saturated carbocyclic ring together with carbon atom 25, the cyclopropyl, cyclopentyl, or cyclohexyl rings are especially preferred.

Preferred according to this invention are 24-homo vitamin D derivatives of general formula I in which:

$R^1$ stands for a hydroxy group or $R^2$ and $R^3$ stand for a methyl group or $R^4$ and $R^5$ stand for a hydrogen atom and n is 1, 2 or 3.

A double bond is preferably between carbon atoms 22 and 23.

Especially preferred are the compounds (5Z,7E,22E)-(1S,3R,24R)-9,10-seco-24a-homo-5,7,10 (19),22-cholestatetraene-1,3,24-triol and (5Z,7E,22E)-(1S,3R,24S)-9,10-seco-24a-homo-5,7,10 (19),22-cholestatetraene-1,3,24-triol. Natural vitamins $D_2$ and $D_3$ or their biologically active metabolites (natural vitamins $D_2$ and $D_3$ are biologically inactive in themselves and become active only after hydroxylation in the 25-position in the liver or in the 1-position in the kidney) exhibit as a characteristic feature a double bond between the positions $C_{10}$ and $C_{19}$, which is considered decisive for vitamin D activity (cf. general formula V). The action of Vitamins $D_2$ and $D_3$ consists of the stabilization of the plasma $Ca^{++}$ and plasma phosphate levels; vitamins $D_2$ and $D_3$ counteract the reduction of plasma $Ca^{++}$ levels.

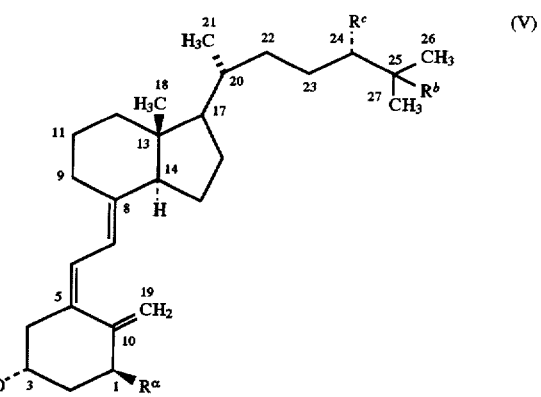

Ergocalciferol: $R^a=R^b=H$, $R^c=CH_3$. Vitamin $D_2$ double bond C 22/23

Cholecalciferol: $R^a=R^b=R^c=H$ Vitamin $D_3$

25-Hydroxycholecalciferol: $R^a=R^c=H$, $R^b=OH$

1α-Hydroxycholecalciferol: $R^a=OH$, $R^b=R^c=H$

1α,25-Dihydroxycholecalciferol: $R^a=R^b=OH$, $R^c=H$ Calcitriol

Besides their marked action on the calcium and phosphate metabolism, vitamin $D_2$ and $D_3$ and its derivatives also have proliferation-inhibiting and cell-differentiating actions (H. F. De Luca, The Metabolism and Function of Vitamin D in Biochemistry of Steroid Hormones, editor H. [two letters illegible] Makin, 2nd Edition, Blackwell Scientific Publications 1984, pp. 71–116). But overdose phenomena (hypercalcemia) can occur with vitamin D use.

1alpha-Cholecalciferols, hydroxylated in the 24 position, as produced from DE AS 25 26 981 have a lower toxicity than the corresponding unhydroxylated 1alpha-cholecalciferol. The hydroxylated compounds show a selective activation of the intestinal calcium absorption and a weaker bone absorption action than 1alpha-cholecalciferol.

The 24-hydroxy vitamin D analogues, described in international patent application WO 87/00834 can be used for treatment of disorders in humans and animals caused by abnormal cell proliferation and/or cell differentiation.

Quite recently a dissociation relative to the properties of bone absorption action and HL 60 cell differentiation was mentioned by De Luca for different 1,25-dihydroxy-homo vitamin D derivatives. The bone absorption action in vitro is in this case a direct measurement for the calcium mobilization in vivo.

SUMMARY OF THE INVENTION

It has now been found that the 24-homo vitamin D derivatives of general formula I according to the invention in comparison with the vitamin D derivative calcitriol (1alpha,25-dihydroxy-cholecalciferol) surprisingly exhibit a more favorable range of action. While the effects on calcium and phosphate metabolism are markedly lessened (reduction of the side effects by overdosing or necessary higher dosage), the proliferation-inhibiting and cell-differentiating actions are approximately maintained (dissociation of effects).

Thus, this invention provides a 24-homo vitamin D derivative of formula I described above.

A process is also provided for producing a 24-homo vitamin D derivative of formula I, wherein a compound of formula IV is converted to a compound of formula III by reduction of the carbonyl group and, optionally, selective hydrogenation of the 22,23-double bond. The compound of formula III is then converted to a compound of formula II by radiation with ultraviolet light to achieve reversal of the stereoisomerism on the 5,6-double bond. The compound of formula II is then converted to a compound of formula I by cleavage of the existing hydroxy protecting groups and, optionally, by partial or complete esterification of the hydroxy groups. Compounds of the formulae I–IV are defined below. Corresponding pharmaceutical preparations contain a 24-homo vitamin D derivative of formula I described above.

The methods of this invention for inhibiting cell proliferation and cell differentiation within a host provide, for example, treatments for psoriasis and malignant tumors.

The vitamin D activity of the compounds according to the invention is determined by the calcitriol receptor test. It is performed by use of a specific receptor protein from the intestines of rachitic chickens. Receptor-containing binding protein is incubated with $^3$H calcitriol (0.5 ng/ml) in a reaction volume of 0.575 ml in the absence and presence of the test substances for one hour in a test tube. A charcoal-dextran absorption is performed for the separation of free and receptor-bound calcitriol. For this purpose, 200 microliters of a charcoal-dextran suspension is fed to each test tube and incubated for 30 minutes at 22° C. Then the samples are centrifuged for 10 minutes at 1500× g at 4° C. The supernatant is decanted and is measured after about 1 hour equilibration in atom light in a beta counter.

The competition curves, obtained for the displacement of $^3$H-labeled reference substance ($^3$H calcitriol) with different concentrations of the test substance as well as of the reference substance (unlabeled calcitriol), are put in relation to one another and competition factor (CF) is determined.

The competition factor is defined as the quotient from the concentrations of the respective test substance and reference substance (unlabeled calcitriol) which are necessary for 50% competition:

$$CF = \frac{\text{Concentration of test substance at 50\% competition}}{\text{Concentration of reference substance (unlabeled calcitriol) at 50\% competition}}$$

A) (5Z,7E,22E)-(1S,3R,24R)-9,10-seco-24a-homo-5,7,10(19),22-cholestatetraene-1,3,24-triol has a CF value of 67, and B) (5Z,7E,22E)-(1S,3R,24S)-9,10-seco-homo-24a-5,7,10(19),22-cholestatetraene-1,3,24-triol has a CF value of 0.8.

For determination of the antiproliferative potency of the compounds according to the invention, the test described below is conducted, individually, with compounds A and B as test substances:

Keratinocytes of newly born mice, with a slight change of the method of Yuspa, S. and Harris, C. C., "Altered differentiation of mouse epidermal cells treated with retinyl acetate in vitro," Exp. Cell Res. 86:95–105, 1974, are prepared and cultivated.

Neonatal NMRI mice of both sexes are killed by decapitation, the skin is removed, washed in an antibiotic-antimycotic solution and incubated with the dermal side downward in dispase II solution (1.20/ml in tissue culture medium M199+25 mmol/l of HEPES+15% fetal calf serum (FCS)+50 U/ml of penicillin/streptomycin (P/S) (preparation medium, PM) at 4° C. overnight. The epidermis is removed and an individual cell suspension is produced by trypsinization. After centrifuging, the cell sediment is resuspended, after trypan blue dyeing, the number of living small round cells is determined and the cells are sown in a density of $4\times10^5$ cells/cm$^2$ in Primaria 24-hole plates in tissue culture medium (M199+15% FCS+50 U/ml of P/S). After 24 hours incubation at 37° C. the cells are washed with phosphate buffered salt solution (PBS) and incubated another 24 hours in serum-free tissue culture medium (M199+50 U/ml of P/S+0.5% of ethanol) with and without test substances at 32.5° C. Then 0.4 microCi/50 microliters of $^3$H methyl thymidine (40 Ci/mmol) is added. After 4 hours the medium is suctioned off and the reaction is ended by addition of 500 microliters of ice-cold 10% trichloroacetic acid (TCA). The cells are washed with TCA and PBS, lysed by incubation in a proteinase K solution (10 mmol/l of tris-HCl, 10 mmol/l of EDTA, 10 mmol/l of NaCl, 0.2% of Triton-X 100, pH 8.0, 50 micrograms/ml of protein kinase K) and the lysate is clarified by centrifuging. In the supernatant the radioactivity is determined scintillation photometrically and, after specific staining of the DNA with diamidinophenylindole (DAPI), the DNA concentration is fluorescence photometrically determined.

Accordingly, calcitriol as well as compounds A and B, depending on the dose, inhibit the $^3$H thymidine incorporation in DNA with approximately the same IC$_{50}$ values given below:

Calcitriol=$2.7\times10^{-9}$ mol/l

Compound A=$6.0\times10^{-9}$ mol/l

Compound B=$9.5\times10^{-9}$ mol/l

By the reduced hypercalcemia risk, the substances according to the invention are suitable in a special way for the production of pharmaceutical agents for the treatment of diseases, which are characterized by an hyperproliferation, e.g., hyperproliferative diseases of the skin (psoriasis) and malignant tumors (myeloid leukemia, skin cancer, colon cancer, mamma carcinoma). It is believed that the target organ should possess calcitriol receptors.

This invention thus also relates to pharmaceutical preparations, which contain at least one compound according to general formula I together with a pharmaceutically compatible vehicle.

The compounds may be administered at dosages from 0.1 µg to 1000 µg/host/day, preferably from 1.0 µg to 1000 µg/host/day to treat malignant diseases. The compounds are administered at a dosage within the range of 0.1 µg to 250 or 500 µg with a pharmaceutically compatible vehicle.

For treatment purposes, the novel compounds of this invention can be formulated, for example, as solutions in innocuous solvents or as emulsions or dispersions in suitable innocuous solvents or carriers, or as pills, tablets, or capsules containing solid carriers according to conventional methods known in the art. For topical applications, the compounds are advantageously formulated as creams or ointments or similar vehicles suitable for topical applications. Any such formulations may also contain other pharmaceutically acceptable and non-toxic excipients such as stabilizers, anti-oxidants, binders, coloring agents, or emulsifying or taste-modifying agents.

The compounds are advantageously administered by injection or by intravenous infusion of suitable sterile solutions or in the form of oral doses via the alimentary canal or topically in the form of ointments, lotions, or in suitable transdermal patches. For the treatment of malignant diseases, the vitamin D compounds of this invention should be administered to subjects in dosages sufficient to inhibit the proliferation of malignant cells and induce their differentiation into normal monocyte-macrophages.

Similarly, for the treatment of psoriasis, the compounds may be administered orally or topically in amounts sufficient to arrest the proliferation of undifferentiated keratinocytes. Suitable dosage amounts are from 0.1–1000 μg of compound per day, such dosages being adjusted, depending on the disease to be treated, its severity, and the response or condition of the subject, as is well understood in the art.

Further, the invention relates to the use of the compounds according to formula I for the production of pharmaceutical agents.

The production of 24-homo vitamin D derivatives of formula I takes place by conversion of a compound of general formula IV

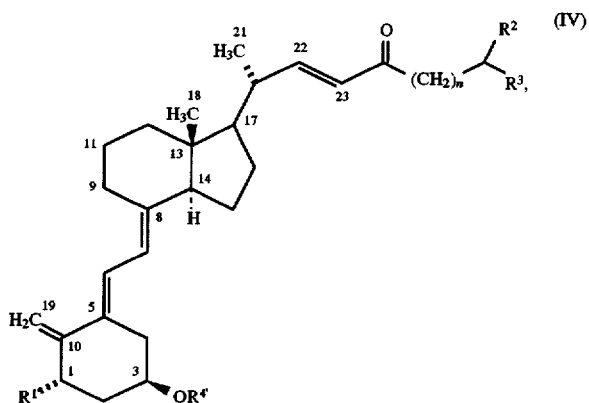

in which

R$^{1'}$ means a hydrogen atom or protected hydroxy group and

R$^{4'}$ means a hydroxy protecting group and

R$^2$ and R$^3$ as well as n have the meaning indicated in formula I.

Selective hydrogenation of the 22,23 double bond in these compounds is optional, after which these compounds are converted to a compound of general formula III, shown below, by reduction of the 24-carbonyl functional group,

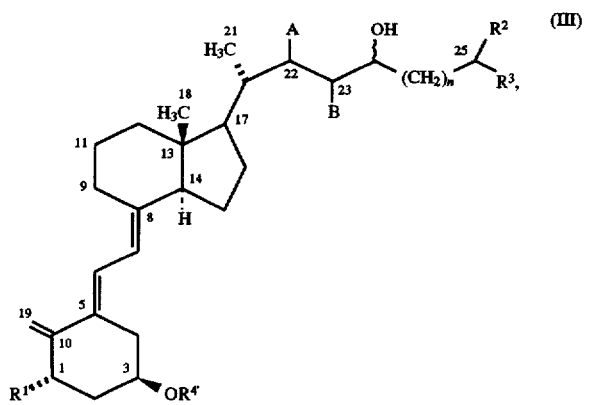

in which R$^{1'}$, R$^{4'}$, R$^2$ and R$^3$ as well as n have the meaning indicated in formula IV and A and B either together mean a second bond or each means a hydrogen atom.

A compound of general formula III is converted to a compound of general formula II, shown below, by radiation with ultraviolet light to achieve reversal of the stereoisomerism on the 5,6-double bond,

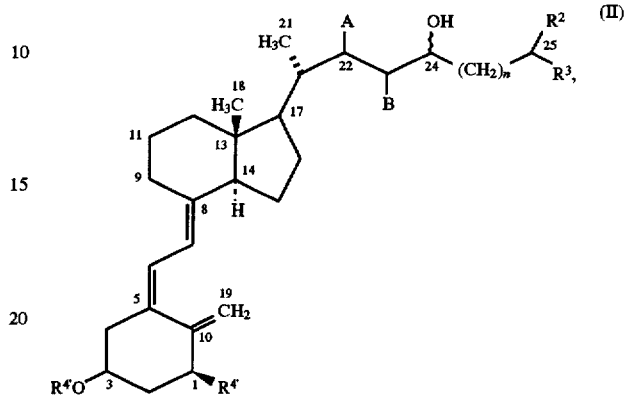

in which

R$^{1'}$, R$^{4'}$, R$^2$ and R$^3$, as well as A and B have the meaning indicated in formula III.

The compound of general formula II is then converted by cleavage of the existing hydroxy protecting groups and optionally by partial or complete esterification of the hydroxy groups to a compound of general formula I.

The reduction of the 24-carbonyl functional group in the compound of general formula IV takes place, for example, with cerium(III) chloride/sodium borohydride in a polar solvent. Both the (24R) and the (24S)-24 hydroxy isomers of general formula III are produced in the reduction. The two isomers can be separated chromatographically.

Optionally, before reduction of the carbonyl function, the C22,C23 double bond can be selectively hydrogenated.

The subsequent conversion of a compound of general formula III to a compound of general formula II takes place, e.g., by radiation with ultraviolet light in the presence of a so-called "triplet sensitizer." In the context of this invention, anthracene is used for this purpose. By cleavage of the pi bond of the 5,6-double bond, rotation of the A ring by 180° around the 5,6-single bond and reestablishment of the 5,6-double bond, the stereoisomerism of the 5,6-double bond is reversed.

Then the existing hydroxy protecting groups are cleaved, preferably with the use of tetra-n-butyl ammonium fluoride. Optionally, the free hydroxy groups are partially or completely esterified with the appropriate carboxylic acid halide (halogen=chloride, bromide) or carboxylic acid anhydride, according to current processes.

The production of the starting compounds of general formula IV starts from the compounds, described in Tetrahedron Letters 43, 4609(1987) or in international patent application WO 87/00834 of Calverley et al., of the type

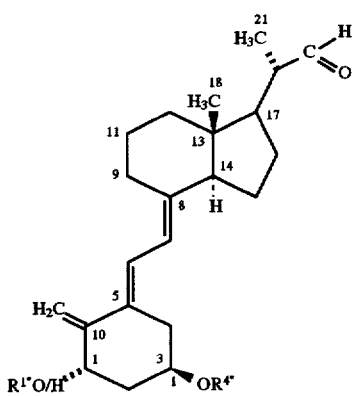

in which the dimethyl tert-butyl silyl radical stands for the hydroxy protecting groups $R^{1"}$ and $R^{4"}$; also other trialkyl silyl radicals are conceivable as protecting groups according to the invention.

Reaction with a phosphorane of formula VI

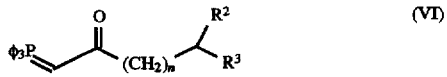

leads to the compounds of general formula IV (Wittig reaction).

The following synthesis examples serve to explain the invention in greater detail.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 39 33 034.6, filed Oct. 2, 1989, are hereby incorporated by reference.

EXAMPLES

Example 1

(5Z,7E,22E)-(1S,3R, 24R)-9,10-seco-24a-homo-5,7,10 (19),22-cholestatetraene-1,3,24-triol 7

Example 2

(5Z,7E,22E)-(1S,3R, 24S)-9,10-seco-24a-homo-5,7,10(19), 22-cholestatetraene-1,3,24-triol 8

I. Isobutylcarbonylmethylenetriphenylphosphorane 1

A. 50 ml of isobutyl methyl ketone in 240 ml of methanol is mixed at 0° C. with 20 ml of bromine and stirred for 1.5 hours more at 10° C. Then 360 ml of water is added and stirred for 16 hours at room temperature. The reaction mixture is mixed with saturated common salt solution, the organic phase is separated and the aqueous phase is extracted with ether. The combined organic phases are washed with 10% sodium carbonate solution and dried on calcium chloride. After filtration, the solvent is evaporated and the residue is distilled. 53.7 g of bromomethyl isobutyl ketone is obtained as colorless oil: $Bp^{15-20}$ 67°–69° C.

B. 53.6 g of bromomethyl isobutyl ketone is added to 78.5 g of triphenylphosphine and the cooled reaction mixture is recrystallized in methylene chloride/ether (1:2). 111.7 g of isobutylcarbonylmethyltriphenylphosphonium bromide with a melting point of 244°–245° C., is obtained.

C. 111.6 g of isobutylcarbonylmethyltriphenylphosphonium bromide in 1500 ml of methylene chloride is mixed with 1500 ml of 2N NaOH and stirred for 30 minutes at room temperature. The organic phase is separated, washed with water and dried on sodium sulfate. After filtration and evaporation of the solvent, the residue is recrystallized in tert-butyl methyl ether. 72.2 g of title compound 1, with a melting point of 120°–121° C., is obtained. By variations of the ketone component in reaction step a), other phosphoranes of the formula can be produced analogously.

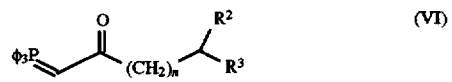

II. (5E,7E,22E)-(1S,3R)-1,3-bis-(tert-butyl-dimethyl silyloxy)-9,10-seco-24a-homo-5,7,10(19)-22-cholestatetraene-24-one 2

8.0 g of (1S,3R)-bis-(tert-butyl dimethyl silyloxy)-(20S)-formyl-9,10-secopregna-(5E,7E,10(19)-triene A (Calverley Tetrahedron 43, 4609 (1967) and 12.0 g of 1 are stirred in 46 ml of dimethyl sulfoxide for 6 hours at 105° C. under nitrogen. The reaction mixture is then diluted at room temperature with ethyl acetate and washed with common salt solution. The organic phase is dried on sodium sulfate and filtered. After removal of the solvent, the residue is filtered with toluene through silica gel. Evaporation of the solvent and gradient chromatography (toluene/hexane (1:1) →toluene) of the residue on silica gel yield 3.6 g of title compound 2 as amorphous solid.

III. (5E,7E,22E)-(1S,3R,24R)-1,3-bis-(tert-butyl-dimethyl silyloxy)-9,10-seco-24a-homo-5,7,10(19)-22-cholestatetraene-24-ol 3

(5E,7E,22E)-(1S,3R,24S)-1,3-bis-(tert-butyl-dimethyl silyloxy)-9,10-seco-24a-homo-5,7,10(19),22-cholestatetraene-24-ol 4

3.5 g of compound 2 in 9 ml of tetrahydrofuran and 20.6 ml of methanol are mixed with 20.6 ml of a 0.4 molar methanol $CeCl_3 \times 7H_2O$ solution. 570 mg of sodium borohydride is added by portions under nitrogen with ice cooling. The suspension is stirred for 40 minutes with ice cooling and then put into ice/common salt solution. The aqueous phase is extracted with ethyl acetate, the organic phase is washed neutral with water and dried on sodium sulfate. Filtration and removal of the solvent yield 3.5 g of oil. By chromatography on silica gel with ethyl acetate/hexane (1:9), 534 mg of 3 and 692 mg of 4 each are obtained as crystallizing oil.

IV. (5Z,7E,22E)-(1S,3R,24R)-1,3-bis-(tert-butyl-dimethyl silyloxy)-9,10-seco-24a-homo-5,7,10(19),22-cholestatetraene-24-ol 5

534 mg of 3 is dissolved in 75 ml of toluene and after addition of 89 mg of anthracene and 1 drop of triethylamine, it is radiated at room temperature for 5 minutes with a high pressure mercury vapor lamp (Heraeus TQ 150) through Pyrex glass. The turbid reaction mixture is filtered, concentrated by evaporation and the residue is chromatographed on silica gel with ethyl acetate/hexane (1:9). 410 mg of title compound 5 is obtained as oil.

V. (5Z,7E,22E)-(1S,3R,24S)-1,3-bis-(tert-butyl-dimethyl silyloxy)-9,10-seco-24a-homo-5,7,10(19),22-cholestatetraene-24-ol 6

Analogously to the conditions for the preparation of compound 5, 500 mg of title compound 6 is obtained as oil from 680 mg of compound 4.

Example 1

(5Z,7E,22E)-(1S,3R,24R)-9,10-seco-24a-homo-5,7,10(19), 22-cholestatetraene-1,3,24-triol-7

200 mg of compound 5 in 8.0 ml of tetrahydrofuran is kept with 1.5 ml of a molar solution of tetrabutylammonium fluoride in tetrahydrofuran for 50 minutes at 60° C. The cooled reaction mixture is diluted with ethyl acetate and washed with sodium bicarbonate solution and common salt solution. The organic phase is washed neutral with water and dried on sodium sulfate. Filtration and evaporation of the solvent yield 210 mg of oil as residue. By chromatography on silica gel with ethyl acetate/hexane (2:1), 124 mg of title compound 7 is obtained as amorphous solid. UV(MeOH) λ=210 (14720), 264 (14240).

Example 2

(5Z,7E,22E)-(1S,3R,24S)-9,10-seco-24a-homo-5,7,10(19), 22-cholestatetraene-1,3,24-triol 8

88 mg of title compound 8, with a melting point of 128°–129° C., is obtained from 200 mg of compound 6 under the conditions of Example 1.

Example 3

(5Z,7E,22E)-(1S,3R,24S)-24-cyclopropylmethyl-9,10-secochola-5,7,10(19),22-tetraene-1,3,24-triol 14

I. (Cyclopropylmethyl)-(triphenylphoshoranylidene) ketone 9

180 mg of lithium chloride and 540 mg of copper(I) chloride are stirred under nitrogen in 9 ml of tetrahydrofuran for 1.5 hours at room temperature. After cooling to 10° C., 15 0 g of (bromomethyl)-(triphenylphosphoranylidene) ketone (M. Le Corre, C. R. Acad. Sc. (C) 273, 81 (1971) in 225 ml of tetrahydrofuran is added and stirred for 30 minutes. Then 29.5 ml of an approximately 1.6 molar solution of cyclopropyl magnesium bromide in tetrahydrofuran is instilled (G. F. Reynolds et al., J. Org. Chem. 23, 1217 (1958)) and stirred for 1.5 hours at the same temperature. For working up, the reaction mixture is poured into ice/saturated ammonium chloride solution and then extracted with ethyl acetate. The organic phase is dried on sodium sulfate and then concentrated by evaporation. Chromatography of the solid residue on silica gel with ethyl acetate/acetone (3:1) indicates 5.6 g of title compound 9, with a melting point of 152° C., is obtained.

II. (5E,7E,22E)-(1S,3R)-1,3-bis-(tert-butyldimethyl silyloxy)-24-cyclopropylmethyl-9,10-secochola-5,7,10(19), 22-tetraene-24-one 10

The reaction and work-up is performed as described in paragraph II of Examples 1 and 2, above.

Batch ingredients: 3.72 g of (20S) formyl compound A (as in Examples 1 and 2); 5.6 g 9; in 21 ml dimethyl sulfoxide.

Yield: 2.2 g of compound 10 is obtained as crystallized oil with a melting point of 97°–98° C.

III. (5E,7Ed,22E)-(1S,3R,24R)-1,3-bis-(tert-butyl-dimethyl silyloxy)-24-cyclopropylmethyl-9,10-secochola-5,7,10(19), 22-tetraene-24-ol 11

(5E,7E,22E)-(1S,3R,24S)-1,3-bis-(tert-butyl-dimethyl silyloxy)-24-cyclopropylmethyl-9,10-secochola-5,7,10(19), 22-tetraene-24-ol 12

The reaction and work-up is performed as described in paragraph III of Examples 1 and 2, above.

Batch ingredients: 2.2 g of compound 10 in 5.8 ml of THF and 13.0 ml of methanol; 13.0 ml of 0.4 molar $CeCl_3 \times 7H_2O$ solution; 359 mg of $NaBH_4$; 2.22 g of oil as crude product.

yield: 1.05 g of 11 (combined with 8); 330 mg of 12 as resin.

Further reaction of compound 12 is described in the following reactions; also, compound 11 can analogously be further processed as described below.

IV. (5Z,7E,22E)-(1S,3R,24S)-1,3-bis-(tert-butyldimethyl silyloxy)-24-cyclopropyl methyl-9,10-secochola-5,7,10(19) ,22-tetraene-24-ol 13

320 mg of compound 22 is dissolved in 45 ml of toluene and after addition of 54 mg of anthracene and 1 drop of triethylamine it is radiated at room temperature for 5 minutes with a high pressure mercury vapor lamp (Heraeus TQ 150) through Pyrex glass. The reaction mixture is concentrated by evaporation and the residue (375 mg)—a mixture of compound 13 and anthracene—is directly reacted with tetrabutylammonium fluoride.

V. (5Z,7E,22E)-(1S,3R,24S)-24-cyclopropylmethyl-9,10-secochola-5,7,10(19)-tetraene-1,3,24-triol 14

375 mg of the residue of compound 13 in 14.2 ml of tetrahydrofuran is kept with 2.39 ml of a 1-molar solution of tetrabutylammonium fluoride in tetrahydrofuran under nitrogen for 60 minutes at 60° C. For working up, the cooled reaction mixture is poured into cold sodium bicarbonate solution and then extracted with ethyl acetate. After drying of the organic phase on sodium sulfate, filtration and evaporation of the solvent yields 400 mg of a resin-like residue. Chromatography on silica gel with ethyl acetate/hexane (2:1) yields 150 mg of title compound 14 with a melting point of 137°–139° C.

Example 4

(5Z,7E,22E)-(1S,3R,24S)-24-isoamyl-9,10-secochola-5,7, 10(19),22-tetraene-1,3,24-triol 16

I. Isoamylcarbonylmethylenetriphenylphosphorane 15

Compound 15 is obtained as a solid with a melting point of 64°–67° C. from isoamylketone analogous to the procedures describes for the production of isobutylcarbonylmethylenetriphenylphosphorane.

II–V Title compound 16 is produced analogously to the sequence described in paragraphs II–V of Example 1 from 5.69 g (20S)-formyl compound A and 8.93 g compound 15. Compound 16 is obtained as a solid with a melting point of 119°–120° C.

Example 5

(5Z,73,22E)-(1S,3R,24S)-cyclopentylmethyl-9,10-secochola-5,7,10(19),22-tetraene-1,3,24-triol 18

I. Cyclopentylmethylcarbonylmethylenetriphenylphosphorane 17

Compound 17 is obtained as crystallized oil with a melting point of 84°–87° C. from cyclopentyl acetone analogously to the procedure described for the production of isobutylcarbonylmethylenetriphenylphosphorane.

II–V. Title compound 18 is produced analogously to the procedures described in paragraphs II–V of Example 1 from 3.50 g (20S)-formyl compound A and 5.68 g of compound 17. Compound 18 is obtained as a solid with a melting point of 90°–93° C.

Example 6

(5Z,7E,22E)-(1S,3R, 24R)-24-(2-ethylbutyl)-9,10-secochola-5,7,10(19),22-tetraene-1,3,24-triol 25

Example 7

(5Z,7E,22E)-(1S,3R,24S)-24-(2-ethylbutyl)-9,10-secochola-5,7,10(19),22-tetraene-1,3,24-triol 26

I. 4-Ethyl-pentanoylmethylenetriphenylphosphorane 19

A. Ethyl-2-butene-1(2)-carbonitrile 19a 170 g of cyanoacetic acid together with 10 g of ammonium acetate and 10 g of acetic acid in 100 ml of benzene are placed in a 1 l flask. 172 g of diethyl acetone are added thereto and refluxed for 18 hours very cautiously with a water separator. After evaporation of the benzene, the residue is transferred into 1000 ml of 2N HCl, extracted with diethyl ether, the organic phase separated, washed with saturated sodium chloride solution, dried on sodium sulfate, and concentrated. The residue is distilled two times at 18 mm/Hg. 96.7 g of compound 19a are obtained as colorless oil. Bp: 66°–68° C.; IR: υ (CN) 2240–2212 cm$^{-1}$.

B. Ethyl-2-butane carbonitrile 19b 96.7 g of 4-ethyl-2-butene-1(2)-carbonitrile 19a are diluted with ethanol to a volume of 150 ml. 2 g Pd/coal (10%) are added and hydrated for 7 hours at 50° C. The reaction mixture is then filtered over celite, concentrated, and 400 ml 2N HCl added, extracted with diethyl ether, dried, concentrated, and distilled under vacuum. 50.5 g of substance 19b are obtained as colorless oil: Bp$^{6-8}$ 45° C.; $^1$H-NMR (300 MHz) [δ] 0.92 (6H,t) 1.5 (5H,m) 2.34 (2H,d).

C. 4-Ethyl-2-hexanone 14.4 g of magnesium shavings, together with 150 ml diethyl ether, are placed in a three-necked flask.

85.2 g methyl iodide in 50 ml of diethyl ether are added dropwise. Thereafter, 100 ml of benzene are added, and a part of the diethylether is distilled off. After addition of 33.3 g of ethyl-2-butyl-carbonitrile 19b, the mixture is heated under reflux for 5 hours. The reaction mixture is hydrolyzed with NH$_4$Cl-solution, extracted with diethyl ether, washed with water, dried over sodium sulfate, concentrated, and distilled in vacuo over a Vigreux column. Obtained are:

12.4 g 19c as a colorless oil;

Bp $^{16}$ 54° C., IR υ (CO) 1730 cm$^{-1}$;

NMR [δ] 0.86 (6H,t) 1.30 (4H,m) 1.80 (1H,m), 2.13 (3H, s) 2.33 (2H,d).

D. Bromomethyl-4-ethyl-pentyl ketone 19d 12 g of 19c in 60 ml of methanol are mixed at 0° C. with 14.8 g of bromine and further stirred for 30 minutes at 0° C. Thereafter, 100 ml of water are added while cooling and stirred for 16 hours at room temperature. The reaction mixture is treated with a saturated solution of sodium chloride, extracted with ether, washed with a saturated solution of sodium bicarbonate, and dried over sodium sulfate. After filtration, the solvent is evaporated and the residue distilled. Obtained are:

13.4 g of 19d;

Bp$^{12}$ 54° C.;

NMR (300 MHz) [δ] 0.86 (6H,t) 1.23 (4H,m) 1.86 (1H,m) 2.58 (2H,d) 3.88 (2H,s).

E. 4-Ethylpentanoylmethyltriphenylphosphonium bromide 13.4 g of 19d are added to 17.3 g of triphenylphosphane. After having been allowed to stand overnight, 76 ml of dichloromethane are added and the mixture refluxed for 30 minutes. After cooling, the reaction mixture is treated with 110 ml of diethyl ether and washed with 80 ml of dichloromethane/diethyl ether (3:5). 26.4 g of the phosphonium bromide 19e are obtained.

NMR (300 MHz) [δ] 0.78 (6H,t) 1.20 (4H,m) 1.77 (1H,m) 2.87 (2H,d) 5.7 (2H, d) 7.78 (15H,m).

F. 4-Ethylpentanoylmethylenetriphenyl phosphorane 19

26 g of compound 19e in 70 ml of methanol are treated with 5.04 g of sodium bicarbonate in 70 ml of water and stirred for 30 minutes at room temperature. The reaction mixture is poured into water, extracted with dichloromethane, the organic phase separated, washed with water, dried over sodium sulfate, and concentrated. The residue is mixed by stirring with ethyl acetate. Obtained are 18.8 g of title compound 19.

NMR (300 MHz) [δ] 0.93 (6H,t) 1.52 (4H,m) 2.31 (1H,m) 2.48 (2H,d) 3.94 (1H, broad d) 7.48 and 7.88 (15H,m).

II. (5E,7E,22E)-(1S,3R)-1,3-bis-(tert-butyl-dimethylsilyloxy)-24-(2-ethyl-butyl)-9,10-secochola-5,7,10(19)22-tetraene-24-one 20

3.4 g of (20S)-formyl compound A and 5.7 g 19 are Warmed in 100 ml of toluene overnight at 80° C. Thereafter, the reaction mixture is added to water, the organic phase separated, washed with a saturated solution of sodium chloride, dried over sodium sulfate, and concentrated. By chromatography of the oil residue on silica gel with toluene, 1.1 g of compound 20 are obtained as an oil.

NMR (300 MHz) [δ] 0.53 (3H,s) 0.79 (24H) 1.2 (3H,d) 4.17 (1H,m) 4.48 (1H,m) 4.81 (2H,d) 5.78 (1H,d) 5.98 (1H,d) 6.39 (1H,d) 5.62 (1H,q).

III. (5E,73,22E)-(1S,3R,24R)-1,3-bis-(tert-butyl-dimethylsilyloxy)-24-(2-ethylbutyl)-9,10-secochola-5,7,10(19)22-tetraene-24-ol 21, and (5E,73,22E)-(1S,3R,24S)-1,3-Bis-(tert-butyl-dimethylsilyloxy)-24-(2-ethylbutyl)-9,10-secochola-5,7,10(19)22-tetraene-ol 22

The reaction and work-up is performed as described in paragraph II of Examples 1 and 2, above.

Batch ingredients: 1.1 g of compound 20 in 2.8 ml THF and 6.3 ml methanol; 920 mg of CeCl$_3$×7H$_2$O in 6.1 ml methanol; 263 mg of NaBH$_4$.

Yield: 340 mg of 21 and 140 mg of 22, each as an oil.

21 and 22: NMR (300 MHz) [δ] 0.50 (3H,s) 0.7–0.88 (24H) 4.05 (1H,m) 4.14(1H,m) 4.48 (1H,m) 4.91 (2H,d) 5.32 (1H,dd) 5.47 (1H,dd) 5.77 (1H,d) 6.40 (1H,d).

IV. (5Z,7E,22E)-(1S,3R,24R)-1,3-bis-(tert-butyldimethylsilyloxy)-24-(2-ethylbutyl)-9,10-secochola-5,7,10(19)22-tetraene-24-ol 23

340 mg of compound 21 is dissolved in 60 ml of toluene, and, after addition of 53 mg of anthracene and 1 drop of triethylamine, it is radiated at room temperature for 5 minutes with a high pressure mercury vapor lamp (Heraeus TQ 150) through Pyrex glass. The turbid reaction mixture is filtered and concentrated. About 340 mg of title compound 23 are obtained.

(5Z,7E,22E)-(1S,3R,24S)-1,3-bis-(tert-butyl-dimethylsilyloxy)-24-(2-ethylbutyl)-9,10-secochola-5,7,10 (19)22-tetraene-24-ol 24

About 130 mg of title compound 24, as oil, is obtained from 130 mg of compound 22 under the conditions under preceding paragraph IV.

V. (5Z,7E,22E)-(1S,3R, 24R)-24-(2-ethylbutyl)-9,10-secochola-5,7,10(19)22-tetraene-1,3,24-triol 25

About 340 mg of compound 23 in 10 ml of tetrahydrofuran is maintained in 2.0 ml of a 1-molar solution of tetrabutylammonium fluoride in tetrahydrofuran for 1 hour at 55° C. The cooled reaction mixture is diluted with ethyl acetate and washed with solutions of sodium bicarbonate and sodium chloride. The organic phase is washed neutral with water, dried on sodium sulfate, and concentrated. After chromatography on silica gel with ethyl acetate and evaporation of the solvent, the residue is mixed by stirring with hexane and filtered. 110 mg of title compound 25 are obtained as amorphous solid with a melting point of 147°–154° C.

(5Z,7E,22E)-(1S,3R,24S)-24-(2-ethylbutyl)-9,10-secochola-5,7,10(19)22-tetraene-1,3,24-triol 26

40 mg of title compound 26, with a melting point of 135°–138° C., is obtained from about 130 mg of compound 24 under the conditions described for the preparation of compound 25.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed:

1. A 24-homo vitamin D derivative of formula I

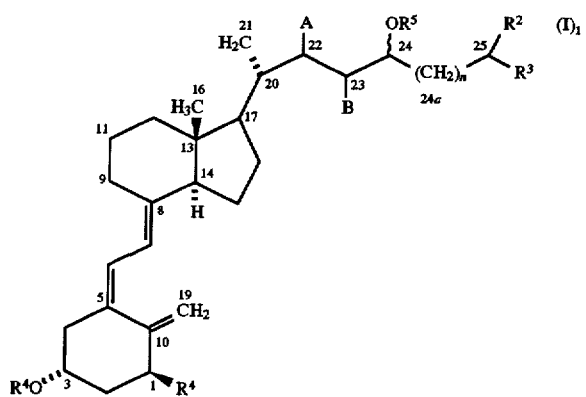

in which $R^1$ is hydrogen, hydroxy, alkanoyloxy of 1 to 8 carbon atoms or benzoyloxy, $R^2$ and $R^3$, independently of one another, each is alkyl of 1 to 4 carbon atoms, or trifluoromethyl or together form a saturated carbocyclic ring of 3 to 9 carbon atoms formed with carbon atom 25, $R^4$ and $R^5$, independently of one another, each is hydrogen, alkanoyl of 1 to 8 carbon atoms or benzoyl, A and B each are hydrogen or together form a second bond, and n is 1, 2, 3, 4 or 5.

2. A 24-homo vitamin D derivative according to claim 1, wherein $R^1$ is a hydroxy group.

3. A 24-homo vitamin D derivative according to claim 1, wherein $R^4$ and $R^5$ each are a hydrogen atom.

4. A 24-homo vitamin D derivative according to claim 1, wherein $R^2$ and $R^3$ each are a methyl group.

5. A 24-homo vitamin D derivative according to claim 1, wherein A and B together stand for a second bond.

6. A 24-homo vitamin D derivatives according to claim 1, wherein n is 1,2 or 3.

7. A 24-homo-vitamin D derivative of formula I

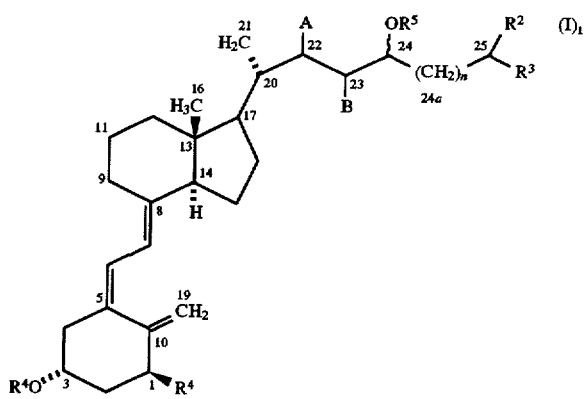

in which $R^1$ is hydroxy, $R^2$ and $R^3$ each are methyl, ethyl, or together form a cyclopropyl, cyclopentyl, or cyclohexyl ring with carbon atom 25, $R^4$ and $R^5$ each are a hydrogen atom, A and B together each are hydrogen or together stand for a second bond and n is 1, 2 or 3.

8. A pharmaceutical composition which comprises a compound of claim 1 and a pharmaceutically compatible vehicle.

9. A method of inhibiting cell proliferation and cell differentiation within a host which comprises administering to a host a compound of claim 1.

10. A method of claim 9, wherein the host has cells with calcitriol receptors.

11. A compound selected from the group consisting of:
(5Z,7E,22E)-(1S,3R,24S)-24-cyclopropylmethyl-9,10-secochola-5,7,10(19),22-tetraene-1,3,24-triol;

(5Z,7E,22E)-(1S,3R24S)-24-isoamyl-9,10-secochola-5,7,10(19),22-tetraene-1,3,24-triol;

(5Z,7E,22E)-(1S,3R,24S)-24-cyclopentylmethyl-9,10,-secochola-5,7,10(19),22-tetraene-1,3,24-triol;

(5Z,7E,22E)-(1S,3R,24S)-24-(2-ethylbutyl)-9,10-secochola-5,7,10(19),22-tetraene-1,3,24-triol; and (5Z,7E,22E)-(1S,3R,24R)-24-(2-ethylbutyl)-9,10-secochola-5,7,10(19),22-tetraene-1,3,24-triol.

12. A pharmaceutical composition which comprises a compound of claim 11 and a pharmaceutically compatible vehicle.

13. A method of treating a malignant tumor within a host which comprises administering a compound of claim 1 to a host afflicted with malignant tumor cells.

14. A method of treating psoriasis which comprises administering a compound of claim 1 to a host afflicted with psoriasis.

15. A method of claim 13, wherein the tumor is located in a locus having calcitriol receptors.

16. A method of claim 14, wherein the host has cells with calcitriol receptors.

* * * * *